United States Patent [19]

Lompe

[11] Patent Number: 4,610,964

[45] Date of Patent: Sep. 9, 1986

[54] NOVEL MICROORGANISM AND ITS USE IN A PROCESS FOR THE PREPARATION OF ALPHA AMYLASE

[75] Inventor: Arved Lompe, Nienburg, Fed. Rep. of Germany

[73] Assignee: Miles Kali-Chemie GmbH & Co. KG, Nienburg, Fed. Rep. of Germany

[21] Appl. No.: 678,468

[22] Filed: Dec. 5, 1984

[30] Foreign Application Priority Data

Dec. 9, 1983 [EP] European Pat. Off. ........ 83112408

[51] Int. Cl.[4] .......................... C12N 9/28; C12N 1/20; C12R 1/125
[52] U.S. Cl. .................................. 435/202; 435/253; 435/839
[58] Field of Search ..................... 435/202, 253, 839

[56] References Cited

FOREIGN PATENT DOCUMENTS 2044513 4/1971 Fed. Rep. of Germany .
2218783 11/1972 Fed. Rep. of Germany .

OTHER PUBLICATIONS

Yoneda, Applied and Environmental Microbiology, Jan. 1980, pp. 274–276.
Qadeer et al, Pakistan J. Sci. Ind. Res., vol. 23, pp. 25–29 (1980).
Microbiology Abstracts, Section A, vol. 14, No. 11, Nov. 1979, p. 9, No. 8298-A-14, London.

*Primary Examiner*—Lionel M. Shapiro
*Attorney, Agent, or Firm*—Schwartz, Jeffery, Schwaab, Mack, Blumenthal & Evans

[57] ABSTRACT

A novel microorganism is disclosed which has the identifying characteristics of *Bacillus subtilis* DSM 2704, including high productivity of alpha amylase.

11 Claims, No Drawings

NOVEL MICROORGANISM AND ITS USE IN A PROCESS FOR THE PREPARATION OF ALPHA AMYLASE

BACKGROUND OF THE INVENTION

The present invention relates to a novel Bacillus strain, *B. subtilis* DSM 2704, and to mutants and recombinants thereof. The present invention further relates to a process for producing alpha amylase, using the aforementioned strain.

Alpha amylase is one of the industrially most important enzymes and is used in large amounts, for example, in the textile and food industries, for the hydrolysis of starch. The industrial production of alpha amylase is thus of substantial economic importance.

In the manufacture of alpha amylase, it is generally known that by fermentation with different types of microorganisms of the genus Bacillus, including *Bacillus subtilis* and its variants, alpha amylase can be obtained in commercially useful amounts. It is particularly advantageous if the fermentation medium itself already contains high concentrations of the active enzyme. There has, therefore, been no lack of effort to obtain, by applying new cultivating and processing techniques, the highest possible enzyme concentration in the fermentation medium. For example, Yoneda et al have described a process using strain of *Bacillus subtilis* which is employed in industry and has been modified by means of a specific transfer of gene fragments to increase the yield of alpha amylase in the fermentation liquor from 130-150 amylase units/ml to 25,000 amylase units/ml, the term "amylase units" having an art-recognized meaning set out in detail below. See APPLIED AND ENVIRONMENTAL MICROBIOLOGY (Vol. 39) 274 et seq. (1980); MOLECULAR CLONING AND GENE REGULATION IN BACILLI (Ganesan et al. eds. 1982). This increase represents an improvement by a factor of about 170 in the production of alpha amylase. Such an increase in productivity is, however, still insufficient for the industrial production of alpha amylase.

SUMMARY OF THE INVENTION

It is therefore an object of the present invention to provide a novel microorganism of the species *Bacillus subtilis* which is characterized, in part, by an enhanced capability to synthesize alpha amylase in culture.

It is another object of the present invention to provide a process for producing commercially useful amounts of alpha amylase via fermentation effected by culturing a novel *Bacillus subtilis* strain.

In accomplishing the foregoing objects, there has been provided, in accordance with the present invention, a biologically pure culture of a *Bacillus subtilis* strain having the identifying characteristics of *Bacillus subtilis* DSM 2704, the strain being capable of producing alpha amylase when cultured in a fermentation medium containing an assimilable source of carbon and an assimilable source of nitrogen. In one preferred embodiment, the aforementioned strain produces alpha amylase in amounts of at least about 200,000 amylase units per ml of the fermentation medium.

There has also been provided in accordance with the present invention a process for producing alpha amylase, comprising the step of culturing, in a fermentation medium containing an assimilable carbon source and an assimilable nitrogen source, a *Bacillus subtilis* strain having the identifying characteristics of *Bacillus subtilis* DSM 2704, such that fermentation in the medium is effected, whereby alpha amylase is produced in the medium. In a preferred embodiment, the fermentation medium comprises a liquid culture medium for the aforementioned strain.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

The novel microorganism of the present invention was observed during quality control examinations, customary in industrial fermentation operations, comprising preparation of smears of samples of the fermentation liquor, fermentation of colonies of such smears in shaker flasks, and preparation of smears of samples of the fermentation liquor from the shaker flask. Thus, the novel *B. subtilis* strain of the present invention was observed as an aberrant colony on the control smear of a sample from a shaker flask, was isolated in biologically pure form by systematic screening, and was then identified as a mutant differing in its morphological and physiological characteristics from the parent species.

The above-mentioned novel microorganism has been deposited with the internal designation A4 under the deposition number DSM 2704 at the Deutsche Sammlung von Mikroorganismen ("German Collection of Microorganisms") since July 29, 1983.

The morphological and metabolic properties of DSM 2704 were investigated and were compared, for determination purposes, with the properties listed in BERGEY'S MANUAL OF DETERMINATIVE BACTERIOLOGY (8th edition, 1974). The following properties were analyzed in detail for the microorganism of the present invention:

Catalase formation: positive
Anaerobic growth in nutrient agar: negative
Gas formation from glucose: negative
Gas formation from xylose: negative
Gas formation from mannitol: negative
Gas formation from arabinose: negative
Gas formation from trehalose: negative
pH on glucose: 6.1
pH on xylose: 6.7
pH on mannitol: 6.1
pH on arabinose: 6.75
pH on trehalose: 6.8
Utilization of propionate: negative
Utilization of citrate: positive
Growth at 65° C.: negative
Growth in nutrient bouillon with 5% NaCl: positive
Growth in nutrient bouillon with 7% NaCl: positive
Growth in nutrient boulillon with 10% NaCl: positive
Voges-Proskauer reaction: positive
pH in V.P. bouillon: 5.45
Growth in 0.001% lysozyme: negative
Growth in 0.02% Na-azide: negative
Hydrolysis of starch: positive
Hydrolysis of hippurate: negative
Decomposition of tyrosine: negative Decomposition of casein: positive
Nitrate reduction: positive
Gelatin liquefaction: more than 1 cm diameter
Egg yolk reaction: negative The morphological characteristics of single cells of DSM 2704 correspond to those associated with *Bacillus subtilis*; similarly, colony morphology is largely identical with that of known strains of *Bacillus subtilis*. In a direct comparison with the parent cultures, the Bacillus strain of the present invention was distinguished by strongly curled colonies with an uneven surface, which in transmitted light was dark brown with a grainy appearance.

By application of the determination table in BERGEY'S MANUAL OF DETERMINATIVE BACTERIOLOGY (8th edition, 1974), the novel strain of the present invention was found to be most similar to *Bacillus subtilis* (Ehrenberg) Cohn. The Bacillus strain of the present invention is, therefore, considered to belong to the species *Bacillus subtilis* (Ehrenberg) Cohn.

The novel microorganism DSM 2704 is far superior to all known microorganisms of the same species and type in the production of alpha amylase. The concentration of alpha amylase in a fermentation media where DSM 2704 is cultivated, in accordance with the present invention, is consistently over 250,000 U/ml, and can exceed 300,000 U/ml where an amylase unit (U) corresponds to a 10% reduction of the iodine starch color complex prepared by the method of Fuwa, described in greater detail below. A particular advantage of the novel microorganism of the present invention is that it forms less protease than the known microorganisms of the species *Bacillus subtilis*. Observed values for protease concentration in fermentation media where DSM 2704 was cultivated, in accordance with the present invention, never exceeded 10 NU/100,000 amylase units. (A protease unit (NU) corresponds to the proteolytic activity required to hydrolyze a predetermined amount of casein under test conditions described in greater detail below.) Typically, the concentration of protease was less than 8 NU/100,000 amylase units.

Mutants, both natural and artificial, and recombinants of the new microorganism *Bacillus subtilis* DSM 2704 can be used to advantage in the alpha amylase production process of the present invention, especially if they produce at least 200,000 U/ml, preferably at least 250,000 U/ml, of alpha amlase during fermentation. Recombinants and mutants of DSM 2704 are particularly suitable if, during fermentation, they produce a maximum of 10 NU of protease per 100,000 amylase units, preferably a maximum of 8 NU per 100,000 amylase units.

Fermentation using *Bacillus subtilis* DSM 2704 to produce alpha amylase according to the present invention can be effected both in liquid culture media and on solid culture media, with liquid cultures generally being preferred. Fermentation is controlled and maintained in accordance with presently available techniques. Similarly, the appropriate nutrient cultures are prepared by known methods. Suitable nutrients contain assimilable carbon sources, assimilable nitrogen sources, and other conventional nutritive and auxiliary substances which favor or are necessary for the growth of Bacillus microorganisms. Various sugars and sugar-containing substances are suitable sources of carbon, and the sugars may be present in different stages of polymerization. The following sugars are exemplary of those suitable for use in the process of the present invention: starch, dextrin, cane sugar, lactose, maltose, fructose, glucose. As sources of nitrogen, inorganic and organic nitrogen compounds may be used, both individually and in combination. Illustrative examples of suitable nitrogen sources include protein-containing substances, such as peptone from soy beans, meat and casein, gelatins, yeast protein or yeast extract, wastes from the processing of meat and animal bodies, and ammonium salts. It is also advantageous that the nutrient media include inorganic salts, in particular alkaline and alkali earth metal salts and phosphates, together with trace elements, such as Fe, Mg, Mn, Co, and Ni.

Fermentation is carried out at pH values between about 5 and 9, preferably between about 6 and 8, and a temperature of 25° to 50° C., preferably 33° to 45° C. The duration of fermentation is between about 30 and about 90 hours, preferably between 50 to 70 hours.

The following examples of fermentation illustrate, without restricting, the alpha amylase-production process of the present invention. To determine alpha amylase activity, the method of Fuwa, *Journal of Biochemistry* (Tokyo) 41: 583 et seq. (1954), was used. High purity amylose (Sigma Chemical Co., Catalog No. A 0512) was used as the enzyme substrate. All other reagents were of standard, analytical grade quality.

Amylose Solution (0.2%)

200 mg of amylose were added to 4 ml of 1 N NaOH solution and allowed to stand overnight in a refrigerator. After dilution to approximately 80 ml the solution was neutralized with 1 N acetic acid and adjusted in volume to 100 ml. It was necessary to prepare this solution fresh daily.

Reagent A

A solution containing 0.2% iodine and 2% potassium iodide was prepared daily from a five times-concentration stock solution by dilution with water.

Analytical technique

500 $\mu$l of 0.5 M acetate buffer and 500 $\mu$l of enzyme-containing solution, optionally diluted with a potassium acetate solution, were mixed with 100 $\mu$l of the amylose solution (0.2%) and incubated for 30 min in a water bath at 37° C.

The reaction was stopped by the addition of 2000 $\mu$l of 1 N acetic acid, the mixture was diluted 1:50 with reagent A, and the extinction coefficient was measured at 700 nm with light path of 10 mm. One amylase unit (U) corresponds to a 10% reduction of the iodine starch color complex thus formed. In the range of 1 to approximately 5 amylase units, the calibrating curve was linear.

Protease activity was determined using the following method:

Casein solution 0.2% casein according to Hammarsten (Merck, Item No. 2242) was dissolved in buffer 1, as described below, by heating to 40° C. for 45 min.

Buffer 1

A solution containing 10.3 g of boric acid, 46.18 g of disodiumhydrogenphosphate $\times$ 7 $H_2O$, and 60.7 g of trisodiumcitrate $\times$ 2 $H_2O$ was adjusted in volume to 2 liters with distilled water (pH = 8.0).

Buffer 2

A solution containing 120 g of sodium acetate×3 H$_2$O and 160 ml of acetic acid was adjusted in volume to 2 liters with distilled water (pH=4.0).

Analytical technique

A control sample, previously denatured by heating, was measured in parallel with the test sample. The control sample and, separately, 50 ml of casein solution (preheated to 40° C.) with 1 ml of enzyme solution were diluted, respectively, so that the activity of the latter was between 0.07 and 0.11 NU/ml. Both were then incubated for 35 min at 40° C.. The resulting reaction in the test sample was stopped by the addition of 25 ml of buffer 2.

After a holding time of 15 min, the test solution was filtered (Blauband, Schleicher and Schull No. 5893).

In the filtrate, nitrogen content was determined by the Kjeldahl method. The protein content was calculated using the following formula:

[protein]=[nitrogen]×6.25.

One protease unit (NU) is defined as the activity which hydrolyzes 40% of the casein under the above-described test conditions of the test.

EXAMPLE 1

To prepare 1 liter of the nutrient culture, 90 g of lactose, 30 g of soy meal, and 10 g of proteosepeptone oxoid No. L46 were, mixed, poured in 50 ml aliquots into separate Erlenmeyer flasks, (triple baffled) sterilized, and inoculated with *Bacillus subtilis* DSM 2704. After 70 hours of fermentation on a circular shaking machine, each aliquot was vigorously centrifuged and the enzymatic activity of the supernatants was determined. On the average alpha amylase activity amounted to about 300,000 U/ml, while protease activity was approximately 21 NU/ml.

EXAMPLE 2

To prepare 1 liter of the nutrient culture, 90 g of maltodextrin, 30 g of soy, 10 g of gelatin, and 2.5 g of diammoniumphosphate were mixed, poured in 50 ml aliquots into separate Erlenmeyer flasks, (triple baffled) sterilized, and inoculated as in Example 1. After fermentation in the manner described in Example 1, the yield of alpha amylase averaged approximately 280,000 U/ml; the protease activity was about 22 Nu/ml.

EXAMPLE 3

The medium described in Example 1 was fermented in a 2 liter fermenter having a useful volume of 650 ml, an air flow of 1.3 v/vm and an agitator rpm of 900$^{-1}$. The yield of alpha amylase after 70 hours of fermentation was 300,000 U/ml; the protease activity was approximately 24 NU/ml.

The processing of the fermented liquor and the recovery of alpha amylase produced according to the present invention were accomplished by generally known methods.

What is claimed is:

1. biologically pure culture of bacterial strain *Bacillus subtilis* DSM 2704, said strain being capable of producing alpha amylase when cultured in a fermentation medium containing an assimilable source of carbon and an assimilable source of nitrogen.

2. A biologically pure culture according to claim 1, wherein said strain produces alpha amylase in amounts of at least about 200,000 amylase units per ml of said fermentation medium.

3. A biologically pure culture according to claim 2, wherein said strain produces alpha amylase in amounts of at least about 250,000 amylase units, and protease in amounts of no more than about 10 protease units/100,000 amylase units, per ml of said fermentation medium.

4. A biologically pure culture according to claim 3, wherein said strain produces no more than about 8 protease units/100,000 amylase units of said protease per ml of said fermentation medium.

5. A process for producing alpha amylase, comprising the step of culturing, in a fermentation medium containing an assimilable carbon source and an assimilable nitrogen source, the bacterial strain *Bacillus subtilis* DSM 2704, such that fermentation in said medium is effected, whereby alpha amylase is produced in said medium.

6. A process according to claim 5, further comprising the step of separating said alpha amylase from said medium.

7. A process according to claim 5, wherein said strain produces alpha amylase in amounts of at least about 200,000 amylase units per ml of said fermentation medium.

8. A process according to claim 7, wherein said strain produces alpha amylase in amounts of at least about 250,000 amylase units, and protease in amounts of no more than about 10 protease units/100,000 amylase units, per ml of said fermentation medium.

9. A process according to claim 8, wherein said strain produces no more than about 8 protease units/100,000 amylase units of said protease per ml of said fermentation medium.

10. A process according to claim 5, wherein said fermentation medium comprises a liquid culture medium for said strain.

11. A process according to claim 5, wherein said fermentation is carried out at a pH between about 6 and about 8, and for a duration between about 50 to about 70 hours.

* * * * *